United States Patent [19]
Gross

[11] Patent Number: 5,823,184
[45] Date of Patent: Oct. 20, 1998

[54] BREATHING CIRCUIT

[75] Inventor: James R. Gross, Wareham, Mass.

[73] Assignee: Tyco International (US) Inc., Exeter, N.H.

[21] Appl. No.: 823,984

[22] Filed: Mar. 25, 1997

Related U.S. Application Data

[63] Continuation of Ser. No. 228,786, Apr. 18, 1994, abandoned.

[51] Int. Cl.$^6$ .................................................. A61M 16/00
[52] U.S. Cl. ............................... 128/294.18; 128/207.14; 128/911; 128/912
[58] Field of Search ......................... 128/203.12, 204.18, 128/207.14, 911, 912, DIG. 26, 205.24, 207.18, 204.24, 204.25

[56] References Cited

U.S. PATENT DOCUMENTS

| | | | |
|---|---|---|---|
| 3,964,488 | 6/1976 | Ring et al. | 128/207.14 |
| 4,463,755 | 8/1984 | Suzuki | 128/911 |
| 4,621,634 | 11/1986 | Nowacki et al. | 128/204.18 |
| 4,637,384 | 1/1987 | Schroeder | 128/204.18 |
| 4,838,258 | 6/1989 | Dryden et al. | 128/205.23 |
| 4,967,744 | 11/1990 | Chua | 128/912 |
| 5,263,941 | 11/1993 | Cockrill | 128/DIG. 26 |
| 5,333,608 | 8/1994 | Cummins | 128/912 |
| 5,404,873 | 4/1995 | Leagre et al. | 128/204.18 |

FOREIGN PATENT DOCUMENTS

| | | | |
|---|---|---|---|
| 402951 | 12/1990 | European Pat. Off. | 128/204.18 |
| 2824799 | 12/1978 | Germany | 128/204.18 |
| 2025239 | 1/1980 | United Kingdom | 128/911 |
| 2169515 | 7/1986 | United Kingdom | 128/207.14 |
| 05277 | 12/1985 | WIPO | 128/204.18 |

*Primary Examiner*—John G. Weiss
*Assistant Examiner*—William J. Deane, Jr.
*Attorney, Agent, or Firm*—David J. Koris

[57] ABSTRACT

The invention features a component which is part of a breathing circuit for directing flow of air to and from a patient, the breathing circuit including an inspiratory tube defining an inspiratory lumen for flow of air to the patient and an expiratory tube defining an expiratory lumen for flow of air from the patient, the tubes being joined via a common wye piece to the component. The component includes each of inner and outer coaxial tubes, the inner tube defining an inner lumen in communication with the inspiratory lumen, the outer tube defining an outer lumen in communication with the expiratory lumen, wherein the outer tube is made from a collapsible and expandable tubing which is sufficiently flexible to assume a bent configuration and sufficiently stable to retain the bent configuration, and thus is virtually unlimited in its positionability with respect to the patient and the bulky portions of the breathing circuit.

18 Claims, 8 Drawing Sheets

# BREATHING CIRCUIT

This application is a continuation of application Ser. No. 08/228,786, filed Apr. 18, 1994, now abandoned.

FIELD OF THE INVENTION

The invention relates generally to breathing circuits in general and in particular to tubing that leads from the breathing circuit wye joint to an endotracheal tube or to the patient directly.

BACKGROUND OF THE INVENTION

A breathing circuit is used to deliver oxygen with anesthetic gases and vapors to a patient while surgical procedures are performed on the patient. Usually, such apparatus provides a mixture of oxygen, with or without nitrous oxide, for inspiration by the patient, and may conventionally include controls for either assisting or controlling breathing, exhaled volume indicators, alarm systems, positive end expiratory pressure ("PEEP") valves, pressure indicators, gas concentration monitors, flow indicators, heated humidifiers for warming and humidifying the breathing gas and tubing for interconnecting these components with each other and with the patient, thereby forming a "patient breathing circuit". Often, the anesthetist who monitors and controls the apparatus must add specific ancillary devices and accessories to the patient breathing circuit, as warranted by factors such as the physiological status of the patient, the nature of the surgical procedure, the anesthetic technique employed, etc.

A typical breathing circuit is composed of two flexible corrugated tubes that connect to a common "wye" piece. The "wye" piece is a joint at which the corrugated tubes converge to form a common conduit accessible to patient breathing. This conduit may be joined via an elbow piece, i.e., a joining piece providing a 90 degree angle, to an endotracheal tube, the endotracheal tube being insertable into the patient's oral or nasal cavity. Alternatively, the elbow may be omitted and the "wye" piece joined directly to the endotracheal tube. In the latter alternative, it is common for the endotracheal tube itself to be bent at an angle. This type of bent endotracheal tube, i.e., a rae tube, is described in U.S. Pat. No. 3,964,488. A rae tube is made of a flexible material having a memory so that the tube will return to its preformed shape following flexure. In the rae tube, there is a pre-formed portion toward the proximal end of the tube that tends to hold the tube in a predetermined configuration and which also functions as an extension to the tube, permitting the bulky connection of the corrugated tubes to be made away from the patient's head and neck, thereby facilitating surgery in these areas.

The invention provides for a breathing circuit component which is an improvement over the rae-type endotracheal tube. The improved breathing circuit component of the invention eliminates the need for an elbow piece or a rae tube in a breathing circuit apparatus; however, it also may be used in conjunction with an elbow piece.

It is an object of the invention to provide an improved circle breathing circuit in which the bulky breathing circuit apparatus is placed at a distance from the patient, thus freeing the area of the patient's head and neck for surgical maneuvers. Another object of the invention is to permit angular adjustment of the patient-end of a breathing circuit apparatus with respect to the remainder of the apparatus. Thus, another object of the invention is to provide both flexibility and stability of adjustment of the breathing circuit apparatus with respect to the patient. Yet another object of the invention to provide for almost unlimited positionability of the breathing apparatus with respect to the patient, and thus also to provide for adaptability to the surgeon's need for an uncluttered surgical field.

SUMMARY OF THE INVENTION

The invention features a component which is part of a breathing circuit for directing flow of air to and from a patient, the breathing circuit including an inspiratory tube defining an inspiratory lumen for flow of air to the patient and an expiratory tube defining an expiratory lumen for flow of air from the patient, the tubes being joined via a common wye piece to the component. The component includes each of inner and outer coaxial tubes, the inner tube defining an inner lumen in communication with the inspiratory lumen, the outer tube defining an outer lumen in communication with the expiratory lumen, wherein the outer tube is made from a collapsible and expandable tubing which is sufficiently flexible to assume a bent configuration and sufficiently stable to retain the bent configuration, and thus is virtually unlimited in its positionability with respect to the patient and the bulky portions of the breathing circuit.

In preferred embodiments of the component of the invention, the outer coaxial tube is a corrugated tube; i.e., it comprises alternating ridges and grooves, and is made of a material having accordion-like folding properties, thus allowing for length-wise expansion and contraction of the tube. As used herein, "accordion-like" properties include the ability to form bends and to become subsequently straightened and bent in another configuration. This property is facilitated by the formation of a cluster of kinks in the tubing on one side of a bend and a corresponding relief of kinking, i.e., more widely-spaced kinks on the opposing side of the bend, e.g., similar to the contraction and expansion and opposing expansion and contraction movement of an accordion.

Preferably, the inner tube is also made from a collapsible and expandable tubing which is sufficiently flexible to assume a bent configuration and sufficiently stable to retain the bent configuration.

The component may also include an endotracheal tube extending from its leading end.

In another aspect, the invention features a flexible, corrugated, elongate tube having a patient end portion adaptable for patient breathing and a machine end portion open for flow of gas therethrough. In this aspect, at least the patient end portion of the tube comprises an accordion-like material that is adaptable to maintain a shape to which it is conformed by virtue of expansion and contraction of the tube along its length. That is, the patient proximal portion of the tube is positionable along its length such that it allows for placement of various components of the breathing circuit, e.g., additional tubes and machines, out of a surgical field which may include the patient's head and neck.

In this aspect of the invention, it is preferred that the flexible, corrugated tube be adaptable as an outer tube to contain an inner coaxial tube.

Thus, the invention also encompasses a flexible, corrugated elongate outer tube containing an inner coaxial tube having a patient end portion adaptable for patient breathing and a machine end portion open for flow of gas therethrough. The inner coaxial tube may also comprise an accordion-like material that is adaptable to maintain a shape to which it is conformed by virtue of expansion and contraction of the inner tube along its length.

Preferably, the machine end portion of the outer tube is adapted to join via a wye piece to an expiratory limb of a breathing circuit, and the inner tube machine end portion is adapted to join via the same wye piece to an inspiratory limb of the breathing circuit.

In yet another aspect, the invention features an improved circle circuit breathing apparatus, comprising an inspiratory tube defining an inspiratory lumen for flow of air to the patient; and an expiratory tube defining an expiratory lumen for flow of air from the patient. The inspiratory and expiratory tubes are joined via a common wye piece to a breathing tube which includes coaxial breathing tubes comprising an outer expiratory tube and an inner inspiratory tube, wherein the outer tube is made from a collapsible and expandable tubing that is sufficiently flexible to assume a bent configuration and sufficiently stable to retain that bent configuration.

Preferred embodiments of the component of the breathing circuit described above are also preferred for the improved breathing circuit apparatus.

The invention also encompasses methods of administering breathing gas to a patient utilizing the apparatuses described herein. For example, such methods may include allowing a patient to breath a gas from a breathing apparatus comprising an inspiratory inner tube of a breathing circuit and an expiratory outer tube of a breathing circuit, wherein the inspiratory and expiratory tubes are coaxial, the inspiratory tube defining an inner lumen and the expiratory tube defining an outer lumen surrounding the inner lumen, wherein the expiratory tube is made from a collapsible and expandable tubing which is sufficiently flexible to assume a bent configuration and sufficiently stable to retain that bent configuration.

Other methods of administering breathing gas to a patient according to the invention include inserting a breathing apparatus into the trachea of a patient, the apparatus comprising each of inner and outer coaxial tubes, the inner tube defining an inner lumen in communication with the inspiratory lumen, the outer tube defining an outer lumen in communication with the expiratory lumen, wherein the outer tube is made from a collapsible and expandable tubing which is sufficiently flexible to assume a bent configuration and sufficiently stable to retain the bent configuration; and supplying breathing gas to the patient.

Yet other methods include administering breathing gas to a patient by positioning a breathing apparatus that is in air communication with the trachea of a patient such that the apparatus does not occlude a surgical field comprising the patient's neck area, the breathing apparatus comprising each of inner and outer coaxial tubes, the inner tube defining an inner lumen in communication with the inspiratory lumen, the outer tube defining an outer lumen in communication with the expiratory lumen, wherein the outer tube is made from a collapsible and expandable tubing which is sufficiently flexible to assume a bent configuration and sufficiently stable to retain that bent configuration; and supplying breathing gas to the patient.

Preferably, the supplying step includes supplying sufficient breathing gas for inspiration by the patient of a volume of gas that is substantially equal to the volume of air exhaled by the patient.

Advantages of the invention is that the improved breathing component of the invention positions the bulky "wye" piece and corrugated breathing tubes at a distance from the patient, and out of the immediate surgical field, and thus provides better access to the patient's head and neck during surgery. The invention is an improvement on the circle circuit breathing design by virtue of the coaxial tubing arrangement. An advantage of this coaxial arrangement is that expiratory gases in the outer tubing surround and thus warm the inspiratory gases in the inner tubing, thus reducing the trauma to the patient of inhaling cold air. The invention combines the advantages of warming of inspiratory gases in its single limb coaxial design with the advantage of almost unlimited positionability of the accordion-like, expandable and contractible tubing.

Further features will become more fully apparent in the following description of the embodiments of this invention and from the appended claims.

DETAILED DESCRIPTION OF THE INVENTION

Figure 1:
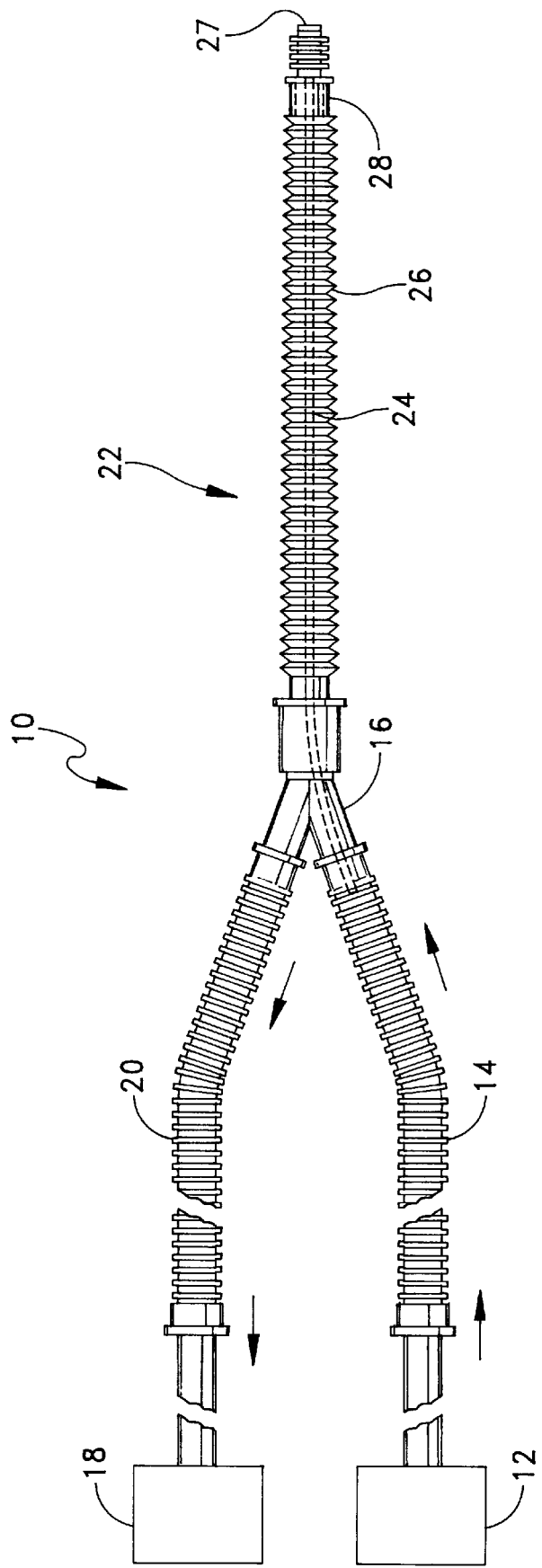
FIG. 1 is a diagram of an improved breathing circuit according to the invention.

FIG. 1 is a diagram showing the arrangement of basic components typically included in a patient breathing circuit having the "circle" configuration. The circuit 10 is connected to an inspiratory valve 12 for controlling the flow of gas to the patient, in air communication through a corrugated hose 14 to the wye joint 16. The circuit also includes an expiratory valve 18 which receives exhaled gases through a corrugated hose 20 which is also connected to the wye joint 16. The circuit may also include various other components, e.g., a gas monitor for providing an indication of the concentration of a specific gas, a pressure gauge for providing an indication of the instantaneous gas pressure, a positive end expiratory pressure ("PEEP") valve for preventing a return to zero pressure when the patient exhales, etc. However, such additional components are not essential to the presentation and are accordingly omitted to avoid obscuring details of the invention.

The invention provides for an expandable breathing circuit limb 22 which includes coaxial inner 24 and outer 26 tubes, the inner tube defining a lumen for the flow of inhaled gas from tube 14 and the outer tube defining a lumen for the flow of exhaled gas through tube 20. The limb 22 is joined via wye joint 16 to the breathing circuit and thus facilitates the flow of breathing gas to and from endotracheal tube adapter 28 (which is inserted into the patient's endotracheal tube) and throughout the breathing circuit in the directions indicated by the arrows.

The outer coaxial tube 26 of the limb 22, and optionally the inner tube 24, will comprise accordion-like, i.e., expandable and contractible, positionable tubing capable of assuming any bent configuration selected by the anesthesiologist and retaining that configuration until positioned into another bent or straight configuration. This tubing is made from any semi-flexible material, e.g., polypropylene, PRO-FAX 6523 homopolymer polypropylene or PRO-FAX 7523 graft copolymer polypropylene (Hercules, Inc.). The corrugated collapsible tubing is constructed in the expanded state, and then subjected to a vacuum, whereby the tube is caused to collapse in upon itself in defined ridges and folds in an accordion-like effect. The collapsed tube thus may expand or contract along its length by virtue of ridging that allows it to fold in upon itself when in the contracted form.

Figure 2:
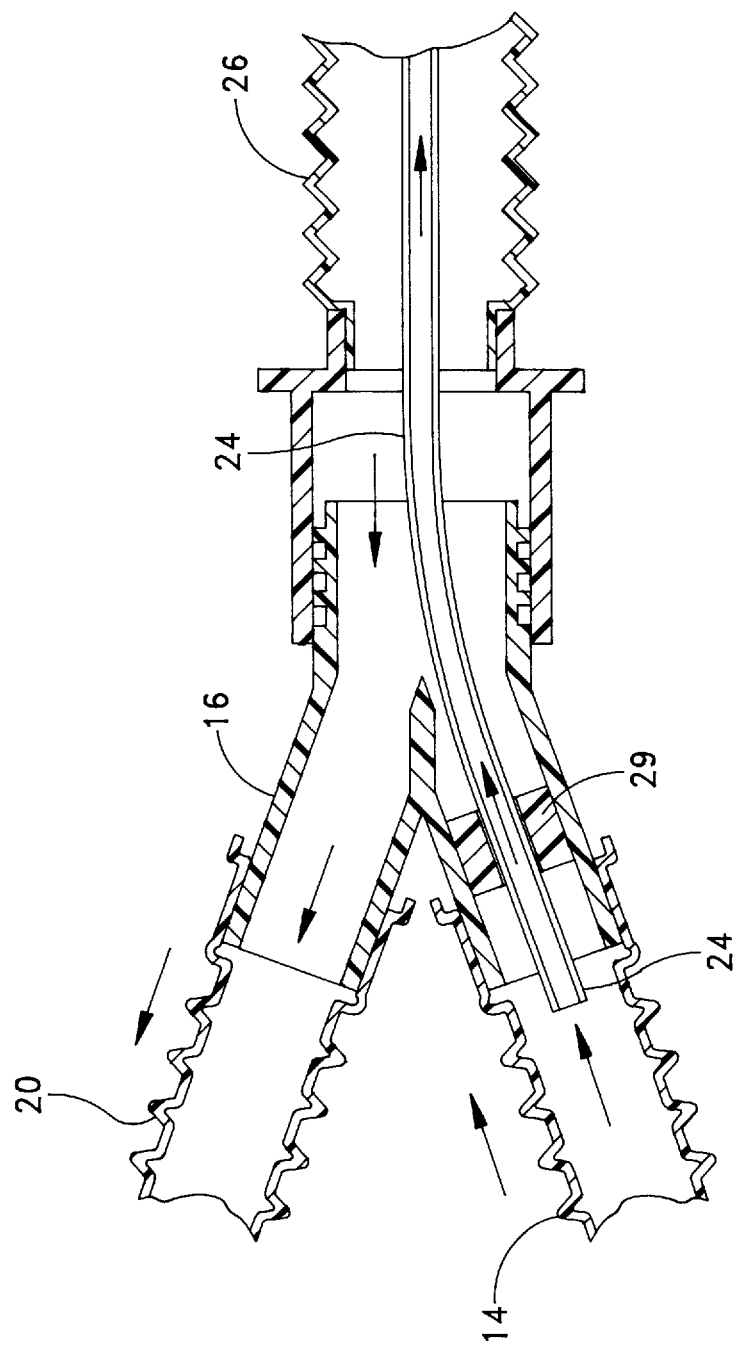
FIG. 2 is an enlarged cross-sectional view of the wye-joint portion of the breathing circuit of FIG. 1, showing directions of air flow through the tubes.
Figure 3:
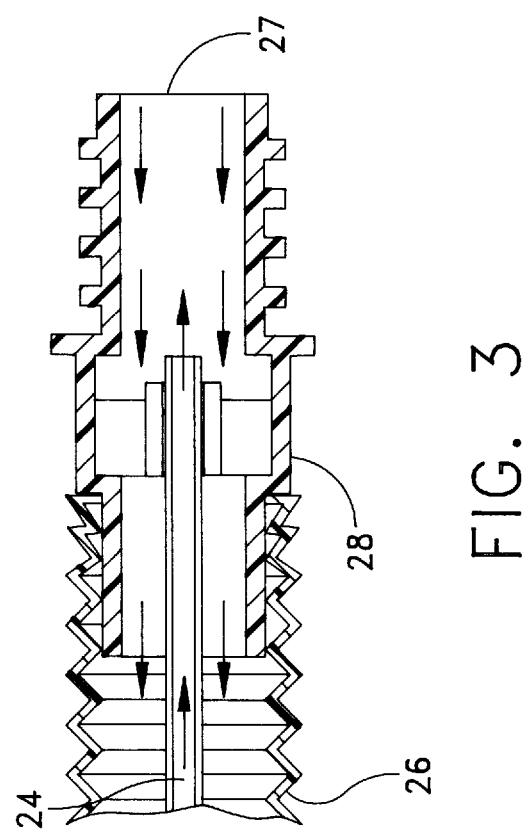
FIG. 3 is an enlarged cross-sectional view of the patient proximal portion of the breathing circuit of FIG. 1, showing directions of air flow through the tubes.

FIGS. 2 and 3 are diagrams of enlarged portions of the improved breathing circuit of the invention of FIG. 1. FIG. 2 is an enlarged cross-sectional view of the portion that includes wye piece 16, in which the directions of air flow, i.e., inspiratory air from tube 14 through inner tube 24, and expiratory air through outer tube 26 to tube 20, are shown. Plug 29 acts as a stopper in that it blocks the flow of inspiratory air through tube 26, and forces the inspiratory air into smaller inner tube 24. FIG. 3 is an enlarged cross-sectional view of the portion of the breathing circuit including adapter 28, in which the directions of air flow, i.e., inspiratory air in inner tube 24 and expiratory air in outer tube 28, are shown. As shown in FIG. 3, the inspiratory and expiratory air is not contained in separate spaces in the extreme patient end portion 27 of the breathing circuit. The slight mixing of inspiratory and expiratory air that may occur during breathing is acceptable in that it resembles the mixing that occurs in a Bain circuit apparatus. End 27 may be connected to an elbow piece 31 and endotracheal tube 33.

Figure 4:
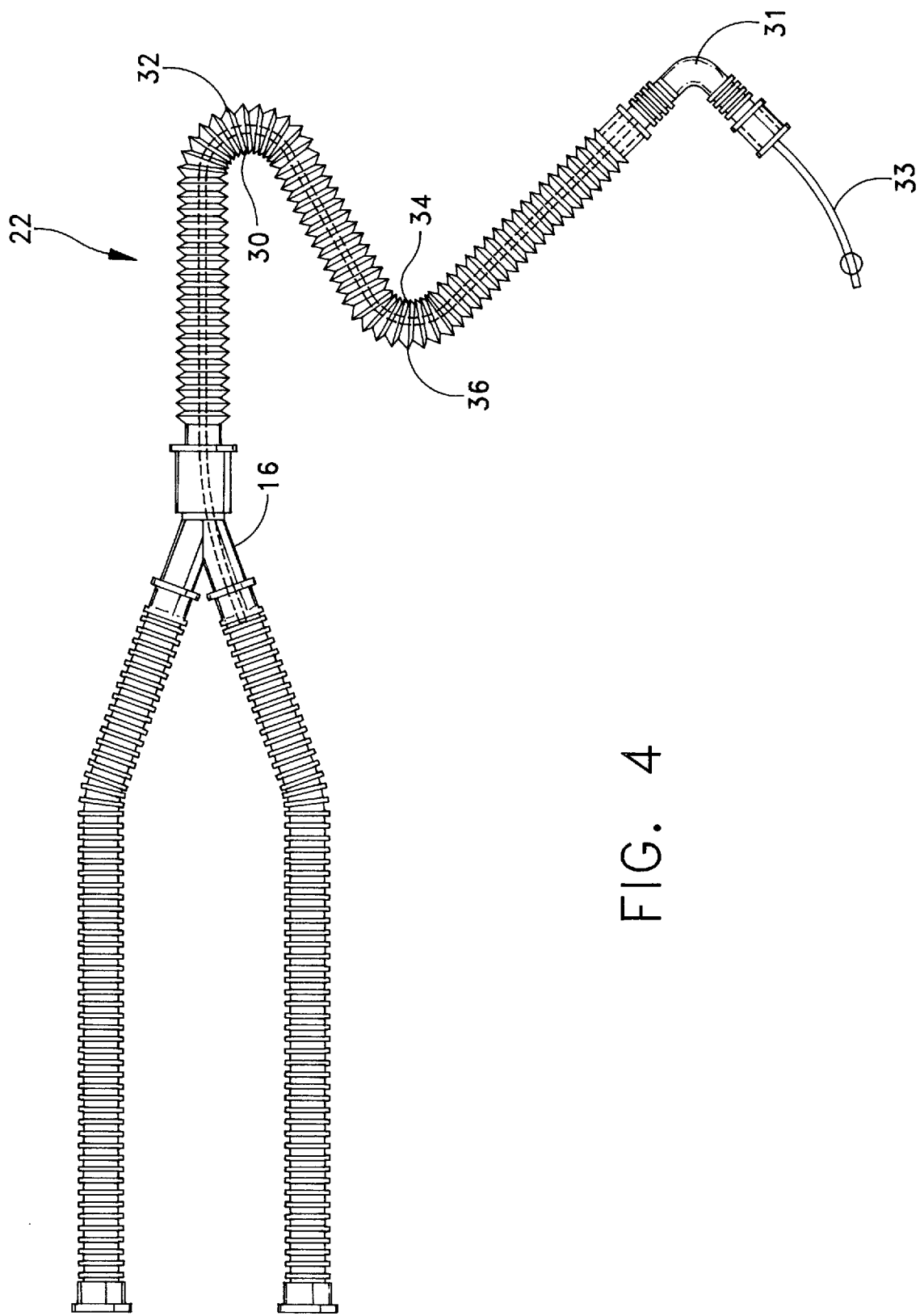
FIG. 4 is a diagram of a portion of the circuit shown in FIG. 1, in which the coaxial limb assumes a bent configuration.

Referring to FIG. 4, the localized kinking of the inner curve 30,34 of a bend and the opposing expansion of the corresponding outer curve 32, 36, respectively, of a bend allows for fine-tuned positionability of bulky portions (e.g., the wye piece and tubing 14 and 20) of the breathing circuit away from the patients' head and neck. The positionability of the expandable/contractible tubing is evident in that the elbow piece 31 and endotracheal tube 33 may be positioned at a chosen distance proximal or distal to wye piece 16. Although only a few embodiments of a chosen distance and configuration of limb 22 is shown herein, it is to be understood that the invention encompasses virtually unlimited positionability of limb 22. Thus, the surgeon or anesthesiologist may choose a configuration of limb 22, including its expanded or contracted configurations, in order to position elbow piece 31 (or endotracheal tube 33) with respect to wye piece 16.

Furthermore, where the inner tube 24 is also an accordion-like tube, albeit of smaller inner diameter, the positionability of the coaxial limb 22 is particularly effectively maintained.

Figure 5:
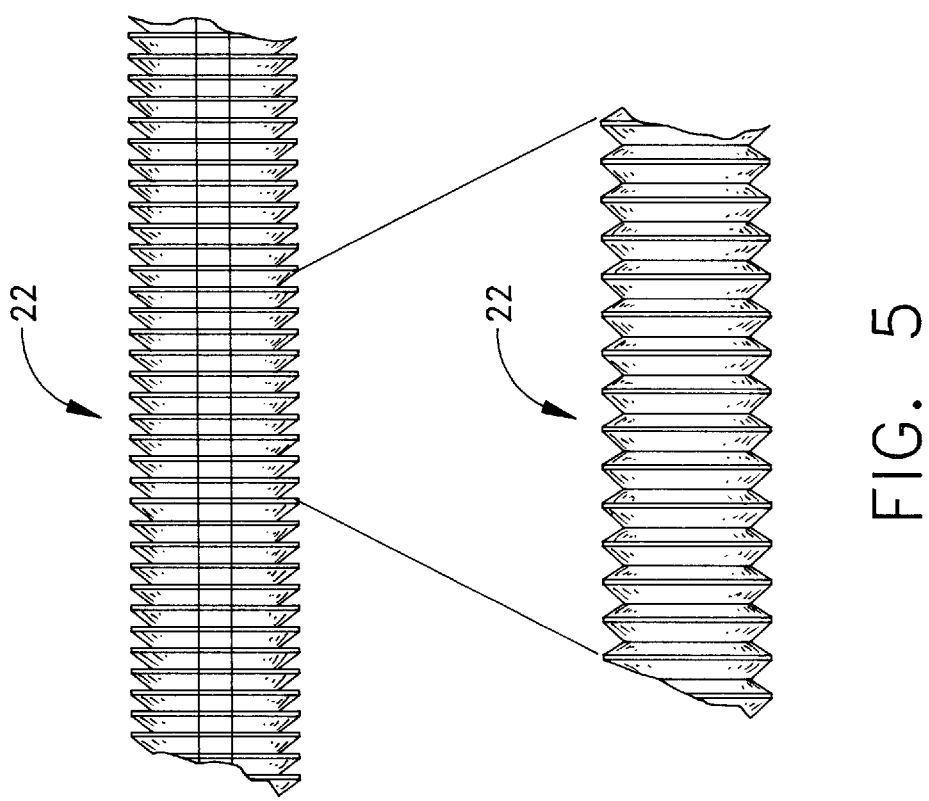
FIG. 5 is a diagram of a portion of the coaxial limb of FIG. 1, in contracted and expanded forms.

Referring to FIG. 5, which illustrates contracted and expanded lengths of a segment of limb 22, respectively, because the accordion-like outer tube 26, and optionally the inner tube 24 also, is exceedingly collapsed in upon itself, the breathing circuit limb 22 also possesses significant additional length that is attainable upon expansion of the tubing 26. As shown in FIG. 5, the contracted tubing includes significantly more length upon expansion than an equivalent length-wise section of non-expandable tubing. The contracted limb 22 may expand to a length that is on the order of two- to five-fold, or even ten- to twenty-fold, its contracted length. This expansion allows for positioning of the bulky breathing apparatus even further away from the patient's head. In the embodiment of the invention in which inner tube 24 is not accordion-like tubing, the inner tube 24 will extend lengthwise into tube 14 such that, upon expansion of outer tube 26, the additional length of inner tube 24 slides out of tube 14 to accommodate length added to limb 22 upon expansion.

The improved breathing circuit limb is used as follows. In operation, fresh gas is introduced into the breathing circuit from valve 12, via hose 16 for patient inspiration via inner tube 24 and adapter 28. During respiration, the patient draws gas from the circuit by inhaling, and a comparable volume of gas flows into tubes 14 and 24 of the circuit to equalize the circuit pressure. When the patient exhales, gas passes through outer coaxial tube 26, into hose 20 and thence to expiratory valve 18. The warm exhaled gas in outer tube 26 surrounds inner tube 24 for a time sufficient to warm the inspiratory gas contained in tube 24.

The invention provides for certain advantages of a Bain breathing circuit in a circle circuit configuration. The circle circuit configuration derives its name from the fact that breathing gas supplied to the patient is constrained to flow continuously, in one direction, around a circuitous path designated by the arrows in FIG. 1. Conventional circle circuits do not include coaxial tubing. However, a Bain breathing circuit which includes coaxial tubing, does not contain a circle of unidirectional flow of gas. Rather, the direction of gas flow in a Bain circuit reverses periodically as the patient inhales and exhales gas. Thus, some mixing of inhaled and exhaled gas occurs in the Bain circuit configuration. Another characteristic distinguishing a Bain circuit configuration from the circle circuit configuration is that, in a Bain circuit, the inspiratory and expiratory breathing hoses are coaxial, whereas they are parallel-connected in the circle circuit.

Because the invention provides coaxial inner and outer tubing, as in the Bain circuit, the warm exhaled gas in the outer tubing envelopes the cooler inhaled gas in the inner tubing, and thus aids in warming the inhaled gas prior to inspiration.

The circle configuration offers a number of advantages. First, since breathing gas may be continuously recycled to the patient, the circle configuration facilitates relatively economical usage of fresh anesthetic gases (some vaporizable agents used in anesthetic procedures are very costly). Second, the circle configuration facilitates relatively rapid patient rebreathing of a comparatively small volume of breathing gas, thereby enabling the patient's alveoli to quickly stabilize the temperature and humidity of the breathing gas and minimizing or eliminating the requirement for further humidification of the anesthetic gases which are dry when initially introduced into the patient breathing circuit. This is a significant advantage because heat and water may be lost through the patient's lungs if the breathing gas supplied to the patient is not heated and humidified to levels approximating conditions in the lung.

The circle configuration lends itself to use in procedures where the patient must be anesthetized for a relatively long time (i.e. for longer than about ½ hour) since the aforementioned advantages take on greater significance in lengthier procedures. More particularly, the aforementioned advantages are not typically obtained if the circle configuration is adopted for procedures of less than about ½ hour's duration. A finite time is required to purge the patient breathing circuit of gases present when the operation starts and to establish a steady state of gas concentration, gas temperature, gas humidity, etc., in the patient breathing circuit and in the patient. Relatively high cost fresh gas must be supplied in the initial stages of the procedure, which tends to eliminate the possibility of economic advantage in a shorter procedure. Further, since the patient's alveoli cannot adequately heat and humidify large volumes of gas introduced over a short time span, external heaters and humidifiers may be required during the initial stages of the procedure to assist in establishing a steady state in the breathing circuit. Because the volume of inspiratory gases is reduced using an inner inspiratory tube of relatively smaller volume in the inventive breathing apparatus, the improved breathing apparatus of the invention is useful in both short and longer anesthetic procedures. Less costly inspiratory gas is needed to fill the inner tubing relative to the conventional circle circuit inspiratory tubing. Thus, the invention retains the advantages of the circle circuit while avoiding its disadvantages, and also provides advantages of the Bain circuit.

Figure 6:
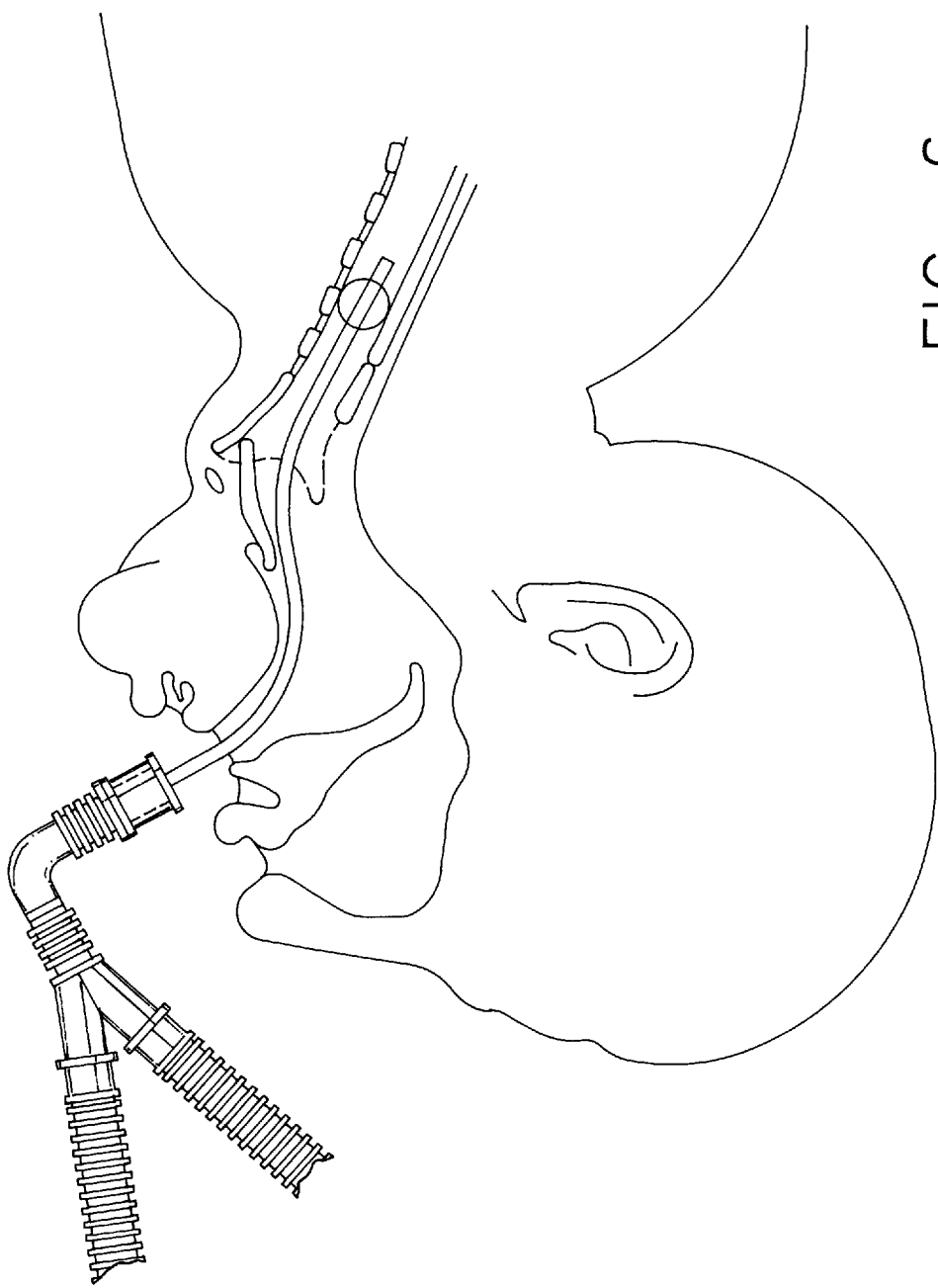
FIG. 6 is a diagram of a prior art breathing circuit, with a standard endotracheal tube inserted into the patient's trachea.
Figure 7:
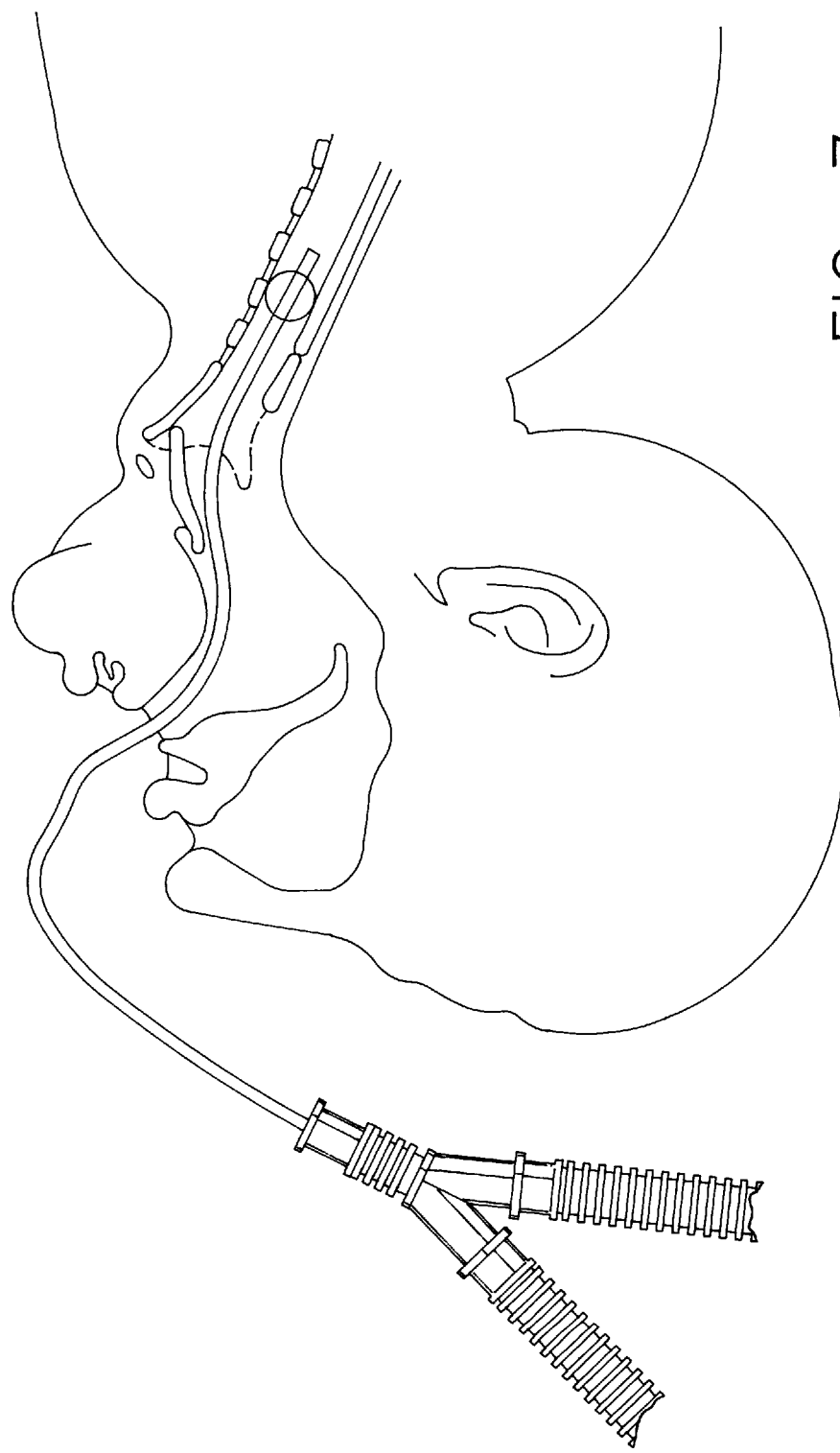
FIG. 7 is a diagram of a prior art breathing circuit connected with a rae tube, with the endotracheal tube portion inserted into the patient's trachea.
Figure 8:
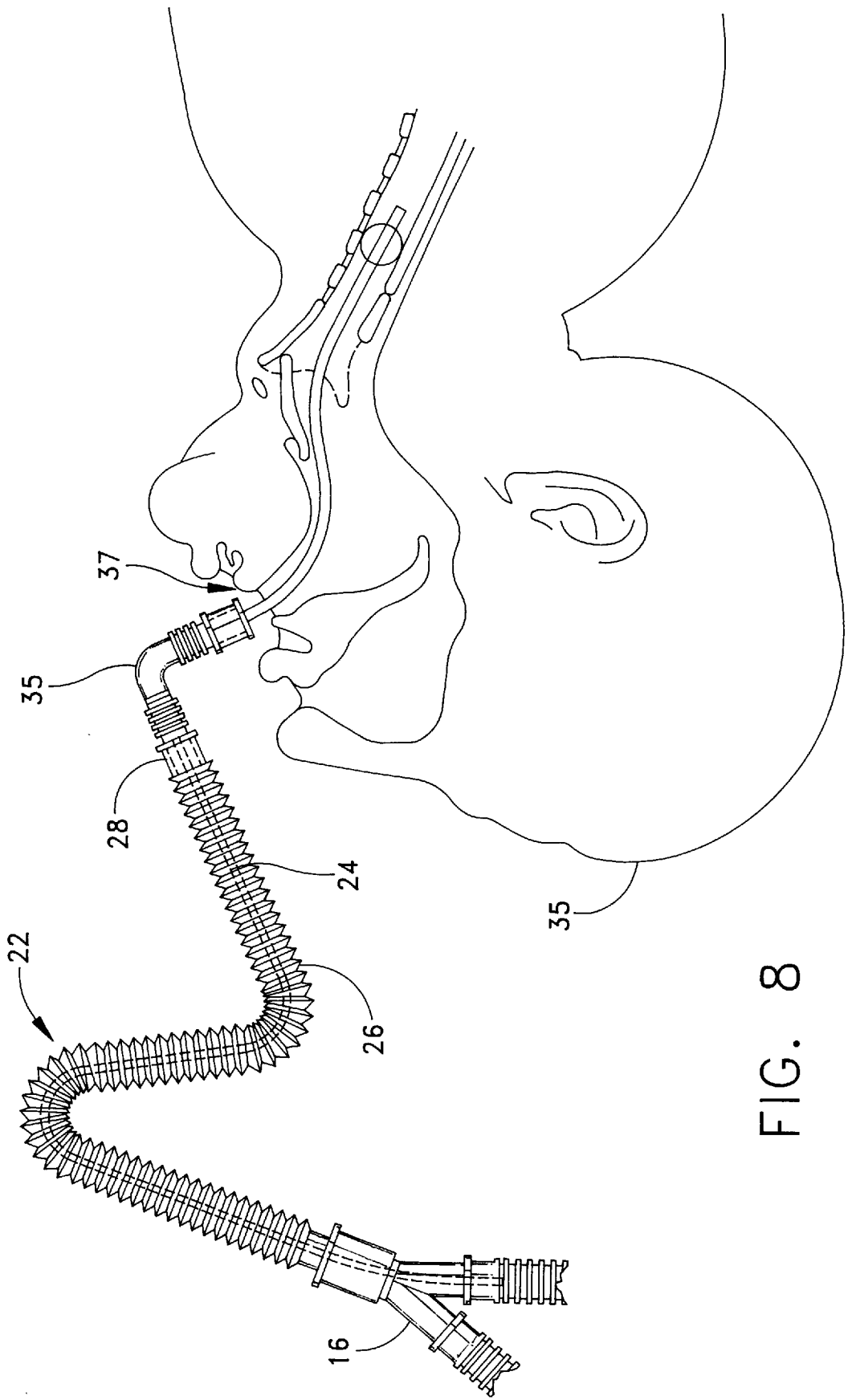
FIG. 8 is a diagram of a portion of the improved breathing circuit of the invention, also with a standard endotracheal tube inserted into the patient's trachea.

FIGS. 6 and 7 illustrate prior art breathing apparatuses in use. For example, in FIG. 6, the wye piece is joined to an elbow piece and endotracheal tube, the tube being inserted into the patient's trachea. It is evident that the prior art apparatus of FIG. 6 positions the bulky wye piece relatively near the patient's head, and therefore-may result in obstruction of the surgeon's access to this area. In the prior art apparatus illustrated in FIG. 7, the bulky wye piece is positioned further away from the patient's head by virtue of an extending tube, e.g., a rae tube. However, the positionability of the wye piece with respect to the patient is limited. In contrast, the improved breathing circuit of the invention, as shown in FIG. 8 in use, provides for virtually unlimited positionability, in that the wye piece 16 may be positioned as chosen by the anesthesiologist with respect to the patient's head 35 and neck area. In this embodiment of the invention, adapter 28 is joined to elbow piece 31, and an endotracheal tube is inserted into the patient's mouth 37. Limb 22 is expandable, contractible, and bendable, such that a selected conformation is retained for any length of time, e.g., particularly the length of time required for any type of surgery. The positionability of limb 22 does not compromise the flow of inspiratory air through inner tube 24 or expiratory air through outer tube 26 during breathing.

OTHER EMBODIMENTS

Other embodiments will be evident to those of skill in the art. It should be understood that the foregoing detailed description is provided for clarity only and is merely exemplary. The spirit and scope of the present invention are not limited thereto, being defined by the claims set forth below.

I claim:

1. A component which is part of a circle circuit breathing circuit for directing flow of air to and from a patient, the breathing circuit including an inspiratory tube defining an inspiratory lumen for flow of air to the patient and an expiratory tube defining an expiratory lumen for flow of air from the patient, said tubes being joined via a wye piece to the component, the component comprising:

each of inner and outer coaxial tubes, said inner tube defining an inner lumen in communication with said inspiratory lumen at the wye piece, said outer tube defining an outer lumen in communication with said expiratory lumen at the wye piece, wherein said outer tube is made from a corrugated tubing which is sufficiently flexible to assume a bent configuration and sufficiently stable to retain said bent configuration about a patient's head and neck area during a surgical procedure, said inner and outer coaxial tubes having a leading end adapted for breathing by a patient, whereby the component is optimally positionable about the patient's head and neck area during the surgical procedure.

2. The component of claim 1 wherein said outer coaxial tube is a corrugated tube having alternating ridges and grooves that are expandable and contractible.

3. The component of claim 1, wherein said inner tube is also made from a collapsible and expandable tubing which is sufficiently flexible to assume a bent configuration and sufficiently stable to retain said bent configuration.

4. The component of claim 1, further comprising an endotracheal tube extending from the leading end of said coaxial tubes.

5. A circle circuit breathing apparatus for administering breathing gas to a patient, comprising:

a flexible, elongate, expiratory tube having a patient end portion of the tube adaptable for patient breathing and a machine end portion of the tube open for flow of gas therethrough, wherein at least the patient end portion of the tube comprises an accordion-like material having a corrugated configuration that is adaptable to maintain a bent or curved configuration to which it is conformed sufficient to allow the patient end portion to be optimally positionable about a patient's head and neck area during a surgical procedure; and a flexible, elongate, inspiratory tube having a patient end portion adaptable for patient breathing and a machine end portion open for flow of gas therethrough, the patient end portion of the inspiratory tube being disposed coaxially within the patient end portion of the expiratory tube;

the machine end portion of the expiratory tube and the machine end portion of the inspiratory tube being joined at a common joint to the coaxially disposed patient end portion of the expiratory tube and the patient end portion of the inspiratory tube.

6. The circle circuit breathing apparatus of claim 5 wherein said inner coaxial tube also comprises an accordion-like material having a corrugated configuration that is adaptable to maintain a selected conformation.

7. The circle circuit breathing apparatus of claim 5 wherein said common joint comprises a wye piece.

8. A circle circuit breathing apparatus, comprising a patient end portion adaptable for patient breathing and a machine end portion open for flow of gas therethrough, wherein said machine end portion comprises:

an inspiratory tube defining an inspiratory lumen for flow of breathing gas out of said inspiratory tube; and an expiratory tube defining an expiratory lumen for flow of exhaled gas into said expiratory tube, said inspiratory and expiratory tubes being joined via a common wye piece to said patient end portion; and said patient end portion comprises coaxial breathing tubes comprising an outer expiratory tube and an inner inspiratory tube, wherein said outer tube is made from a corrugated tubing that is sufficiently flexible to assume a bent configuration and sufficiently stable to retain said bent configuration and to allow the patient end portion to be optimally positionable about a patient's head and neck area during a surgical procedure.

9. The circle circuit breathing apparatus of claim 8 wherein said corrugated tube is made of a material having accordion-like folding properties, thus allowing for said tube to assume and retain said bent configuration.

10. The circle circuit breathing apparatus of claim 8, wherein said inner tube is also made from a corrugated tubing which is sufficiently flexible to assume a bent configuration and sufficiently stable to retain said bent configuration.

11. A method of administering breathing gas to a patient during a surgical procedure, comprising:

providing a circle circuit breathing apparatus comprising a patient end portion adaptable for patient breathing and a machine end portion open for flow of gas therethrough, wherein said machine end portion comprises:

an inspiratory tube defining an inspiratory lumen for flow of breathing gas out of said inspiratory tube, and an expiratory tube defining an expiratory lumen for flow of exhaled air into said expiratory tube, said inspiratory and expiratory tubes being joined via a common joint to said patient end portion; and said patient end portion comprises coaxial breathing tubes comprising an outer expiratory tube and an inner inspiratory tube, wherein said outer tube is made from a corrugated tubing that is sufficiently flexible to assume a bent configuration and sufficiently stable to retain said bent configuration;

optimally positioning said patient end portion about a patient's head and neck area; and allowing breathing by the patient of gas from said breathing apparatus.

12. The method of claim 11, wherein in said providing step, said inner tube of said breathing apparatus is also made from a collapsible and expandable tubing which is sufficiently flexible to assume a bent configuration and sufficiently stable to retain said bent configuration.

13. A method of administering breathing gas to a patient during a surgical procedure, comprising:

providing a circle circuit breathing apparatus in respiratory communication with the trachea of a patient, said apparatus comprising a patient end portion adaptable for patient breathing and a machine end portion open for flow of gas therethrough, wherein said machine end portion comprises:

an inspiratory tube defining an inspiratory lumen for flow of air out of said inspiratory tube, and an expiratory tube defining an expiratory lumen for flow of air into said expiratory tube, said inspiratory and expiratory tubes being joined via a common joint to said patient end portion; and said patient end portion comprises coaxial breathing tubes comprising an outer expiratory tube and an inner inspiratory tube, wherein said outer tube is made from a corrugated tubing that is sufficiently flexible to assume a bent configuration and sufficiently stable to retain said bent configuration;

optimally positioning said patient end portion about said patient's head and neck area; and supplying breathing gas to said patient via said breathing apparatus.

14. The method of claim 13, wherein in said inserting steps, said inner tube of said breathing apparatus is also made from a collapsible and expandable tubing which is sufficiently flexible to assume a bent configuration and sufficiently stable to retain said bent configuration.

15. The method of claim 13, wherein said supplying step includes supplying a sufficient volume of breathing gas to said inspiratory lumen, said volume of gas being substantially equal to a volume of air exhaled by said patient.

16. A method of administering breathing gas to a patient during a surgical procedure, comprising:

providing a circle circuit breathing apparatus in respiratory communication with the trachea of a patient, said apparatus comprising a patient end portion adaptable for patient breathing and a machine end portion open for flow of gas therethrough, wherein said machine end portion comprises:

an inspiratory tube defining an inspiratory lumen for flow of air out of said inspiratory tube, and an expiratory tube defining an expiratory lumen for flow of air into said expiratory tube, said inspiratory and expiratory tubes being joined via a common joint to said patient end portion, and said patient end portion comprises coaxial breathing tubes comprising an outer expiratory tube and an inner inspiratory tube, wherein said outer tube is made from a corrugated tubing that is sufficiently flexible to assume a bent configuration and sufficiently stable to retain said bent configuration;

positioning said breathing apparatus in respiratory communication with the trachea of a patient such that the patient end portion of said apparatus does not occlude a surgical field comprising the patient's head and neck area; and supplying breathing gas to said patient via said breathing apparatus.

17. The method of claim 16, wherein in said positioning step, said inner tube of said breathing apparatus is also made from a collapsible and expandable tubing which is sufficiently flexible to assume a bent configuration and sufficiently stable to retain said bent configuration.

18. The method of claim 16, wherein said supplying step includes supplying a sufficient volume of breathing gas to said inspiratory lumen, said volume of gas being substantially equal to a volume of air exhaled by said patient.

* * * * *